(12) United States Patent
Wachtel et al.

(10) Patent No.: US 10,155,094 B2
(45) Date of Patent: Dec. 18, 2018

(54) INHALER

(75) Inventors: Herbert Wachtel, Ingelheim am Rhein (DE); Andree Jung, Ingelheim am Rhein (DE)

(73) Assignee: Boehringer Ingelheim International GmbH, Ingelheim am Rheim (DE)

( * ) Notice: Subject to any disclaimer, the term of this patent is extended or adjusted under 35 U.S.C. 154(b) by 403 days.

(21) Appl. No.: 13/703,998

(22) PCT Filed: Jun. 1, 2011

(86) PCT No.: PCT/EP2011/059091
§ 371 (c)(1),
(2), (4) Date: May 7, 2013

(87) PCT Pub. No.: WO2011/157561
PCT Pub. Date: Dec. 22, 2011

(65) Prior Publication Data
US 2013/0269685 A1    Oct. 17, 2013

(30) Foreign Application Priority Data

Jun. 18, 2010 (EP) .................................... 10006334

(51) Int. Cl.
*A61M 15/00* (2006.01)
*B05B 11/00* (2006.01)
(Continued)

(52) U.S. Cl.
CPC ........ *A61M 15/0091* (2013.01); *A61M 11/02* (2013.01); *A61M 15/008* (2014.02);
(Continued)

(58) Field of Classification Search
CPC .. A61M 15/00; A61M 15/008; A61M 15/009; A61M 15/0065; A61M 2205/52;
(Continued)

(56) References Cited

U.S. PATENT DOCUMENTS 5,363,842 A * 11/1994 Mishelevich et al. ... 128/200.14
5,833,088 A    11/1998 Kladders
(Continued)

FOREIGN PATENT DOCUMENTS

EP    1970087 A2    9/2008
JP    07509378 A    10/1995
(Continued)

OTHER PUBLICATIONS

International Search Report for PCT/EP2011/059091 dated Aug. 11, 2011.
(Continued)

*Primary Examiner* — Gregory Anderson
*Assistant Examiner* — Elliot S Ruddie
(74) *Attorney, Agent, or Firm* — Philip I. Datlow

(57) ABSTRACT

An inhaler is proposed having an insertable container and a monitoring device for counting uses of the inhaler. The monitoring device is arranged in a detachable housing part or fitted onto a mouthpiece of the inhaler. A supply air current is detected by means of a pressure sensor. A position sensor may further be provided.

26 Claims, 6 Drawing Sheets

(51) Int. Cl.
*A61M 11/02* (2006.01)
*B05B 12/00* (2006.01)
*B05B 12/12* (2006.01)
*A61M 16/00* (2006.01)
*B05B 12/02* (2006.01)

(52) U.S. Cl.
CPC .... *A61M 15/0065* (2013.01); *A61M 15/0083* (2014.02); *B05B 11/0024* (2013.01); *B05B 11/308* (2013.01); *A61M 2016/0021* (2013.01); *A61M 2016/0027* (2013.01); *A61M 2205/332* (2013.01); *A61M 2205/3553* (2013.01); *B05B 11/0037* (2013.01); *B05B 11/0043* (2013.01); *B05B 11/3091* (2013.01); *B05B 12/008* (2013.01); *B05B 12/02* (2013.01); *B05B 12/12* (2013.01)

(58) Field of Classification Search
CPC ...... A61M 2016/0018; A61M 15/0091; A61M 11/02; A61M 2016/0021; A61M 2016/0027; A61M 2205/332; A61M 2205/3553; B05B 11/308; B05B 11/0024; B05B 11/0037; B05B 11/0043; B05B 11/3091; B05B 12/008; B05B 12/02; B05B 12/12
USPC ............ 128/200.14, 200.21, 200.23, 203.22, 128/204.23, 205.24; 222/41, 42; 239/71
See application file for complete search history.

(56) References Cited

U.S. PATENT DOCUMENTS

| | | |
|---|---|---|
| 6,651,658 B1 | 11/2003 | Hill |
| 6,723,077 B2 | 4/2004 | Pickup |
| 6,988,496 B1 | 1/2006 | Kladders |
| 6,990,975 B1 | 1/2006 | Jones |
| 7,231,919 B2 | 6/2007 | Giroux |
| 7,500,444 B2 | 3/2009 | Bonney |
| 7,544,190 B2 | 6/2009 | Pickup |
| 7,802,568 B2 | 9/2010 | Kladders |
| 7,849,851 B2 | 12/2010 | Wuttke |
| 8,616,199 B2 | 12/2013 | Hamano |
| 8,833,364 B2 | 9/2014 | Buchberger |
| 8,960,189 B2 | 2/2015 | Morrison |
| 8,997,735 B2 | 4/2015 | Zierenberg |
| 9,364,619 B2 | 6/2016 | Overfield |
| 2003/0065294 A1 | 4/2003 | Pickup |
| 2005/0228341 A1 | 10/2005 | Edgerley |
| 2005/0247305 A1* | 11/2005 | Zierenberg et al. ..... 128/200.14 |
| 2006/0016449 A1 | 1/2006 | Kladders |
| 2007/0062519 A1* | 3/2007 | Wuttke ............ A61M 15/0065 128/200.14 |
| 2009/0156952 A1 | 6/2009 | Hunter |
| 2009/0209938 A1 | 8/2009 | Aalto-Setaelae |
| 2011/0048415 A1 | 3/2011 | Zierenberg et al. |

FOREIGN PATENT DOCUMENTS

| | | |
|---|---|---|
| JP | 2002537951 A | 11/2002 |
| JP | 2005503899 A | 2/2005 |
| JP | 2005506154 A | 3/2005 |
| JP | 2007522899 A | 8/2007 |
| JP | 2008259818 A | 10/2008 |
| JP | 2009273899 A | 11/2009 |
| JP | 2010036049 A | 2/2010 |
| WO | 9312823 A2 | 7/1993 |
| WO | 199606011 A2 | 2/1996 |
| WO | 199748431 A2 | 12/1997 |
| WO | 2000049988 A2 | 8/2000 |
| WO | 0053247 A1 | 9/2000 |
| WO | 03026559 A2 | 4/2003 |
| WO | 03028797 A1 | 4/2003 |
| WO | 2003035151 A1 | 5/2003 |
| WO | 2004001664 A1 | 12/2003 |
| WO | 2005080001 A1 | 9/2005 |
| WO | 2008142015 A2 | 11/2008 |
| WO | 2009047173 A2 | 4/2009 |
| WO | 2009155581 A1 | 12/2009 |
| WO | 2010045671 A1 | 4/2010 |
| WO | 2010067240 A1 | 6/2010 |
| WO | 2011157561 A1 | 12/2011 |

OTHER PUBLICATIONS

European Search Report for corresponding EP Application No. EP16020261, 9 pages, dated Nov. 16, 2017.

Decision for Final Rejection for corresponding JP Application No. 2016-247353, 5 pages, dated Oct. 8, 2018.

\* cited by examiner

INHALER

The present invention relates to an inhaler for a fluid having a preferably insertable container containing the fluid and having a monitoring device for detecting use of the inhaler, characterised in that the monitoring device has a pressure sensor for measuring the air pressure in the inhaler or the monitoring device for detecting inhalation and/or a position sensor for detecting a position, orientation and/or acceleration of the inhaler, particularly to determine a path of movement of the inhaler.

WO 2005/080001 A1 discloses an inhaler having a monitoring device for detecting actuations. The known inhaler comprises, as a reservoir for a medicament preparation that is to be nebulised, a rigid insertable container having an inner bag containing the medicament preparation and a pressure generator having a drive spring for conveying and nebulising the medicament preparation. Nebulisation is carried out without the use of a propellant gas, namely by the force of the drive spring. The drive spring can be tensioned by rotating an actuating member in the form of a lower housing part of the inhaler and the medicament preparation can be sucked into a pressure chamber of the pressure generator. After manual operation of a blocking element, the medicament preparation in the pressure chamber is put under pressure by the drive spring and atomised, i.e. expelled, forming an aerosol. During the tensioning, on the one hand, and the subsequent nebulisation, on the other hand, the container performs a lifting movement each time. The monitoring device is installed in the lower housing part and may comprise a flow sensor in a mouthpiece of the inhaler for detecting a stream of supply air and hence an inhalation.

The aim of the present invention is to provide an inhaler having an improved and/or simplified monitoring device, particularly allowing improved reliability in use and/or more information as to the user and/or improved monitoring of the user.

The above aim is achieved by an inhaler for a fluid having a preferably insertable container containing the fluid and having a monitoring device for detecting use of the inhaler, characterised in that the monitoring device has a pressure sensor for measuring the air pressure in the inhaler or the monitoring device for detecting inhalation and/or a position sensor for detecting a position, orientation and/or acceleration of the inhaler, particularly to determine a path of movement of the inhaler.

The above aim may be further achieved by an inhaler for a fluid according to the embodiment above, characterised in that the monitoring device comprises a sensor for waking up or switching on the monitoring device in the event of tensioning of a drive spring of the inhaler or when a certain container position is reached.

The above aim may be still further achieved by an inhaler according to one of the preceding embodiments, having a mouthpiece (comprising at least one supply air opening for expelling nebulised fluid, characterised in that the monitoring device is constructed so as to cover the at least one supply air opening and/or to form a supply air pathway and/or can be placed or fitted onto the mouthpiece.

Advantageous further features are described herein.

According to one aspect of the present invention, the monitoring device comprises a pressure sensor for measuring the air pressure in a housing of the inhaler or the monitoring device, particularly in a mouthpiece of the inhaler, for detecting inhalation. This results in a very simple design that is cheap to produce. In particular, a pressure sensor of very simple construction can be used instead of a flow sensor. Moreover, the pressure sensor can be arranged separately from the mouthpiece, in particular outside the mouthpiece, but preferably within the inhaler in another region, most preferably in the lower actuating or housing part. This preferred arrangement of the pressure sensor outside a path for supply air allows a particularly simple construction.

According to another aspect of the present invention, the monitoring device comprises at least one position sensor for detecting a position, orientation and/or acceleration of the inhaler. This allows improved monitoring of actual use. In particular it makes it possible to determine a path of movement of the inhaler. According to another aspect of the present invention, the monitoring device comprises a sensor or switch for waking up, activating or switching on the monitoring device particularly during tensioning of a drive spring of the inhaler or when a particular container position is reached or during other activation of the inhaler for use, for example when opening a mouthpiece cover. This results in a particularly low-energy or low-powered mode of operation. In particular, the monitoring device is at least substantially switched on or woken up or activated only when the inhaler is actually about to be used or being used. Accordingly it is readily possible to achieve increased security of use or increased security in user monitoring.

Preferably, the inhaler or the monitoring device is designed so that after use has ended or a use has been detected, particularly after an inhalation, and optionally also after a predetermined length of time, the monitoring device is switched off or deactivated or switched to standby mode, particularly automatically.

According to another aspect of the present invention, the monitoring device is designed to cover one or more supply air openings in the inhaler, particularly supply air openings in a mouthpiece of the inhaler, and/or to form a supply air pathway, particularly preferably the only supply air pathway of the inhaler. This makes it possible in particular to fit the monitoring device to existing inhaler constructions. Thus, a stream of supply air during inhalation can be very easily measured or detected outside a mouthpiece or inhaler and in this way use of the inhaler can be detected or determined.

According to another aspect of the present invention, the monitoring device can be placed or fitted onto the mouthpiece. In particular, the monitoring device comprises a separate housing that is detached from or detachable from the inhaler. This allows easy modification of existing inhaler constructions and/or easy separation of the monitoring device, for example in order to read out data from the monitoring device.

According to an alternative aspect of the present invention, the monitoring device is mounted on a detachable housing part of the inhaler, particularly firmly connected thereto, preferably installed therein, for example cast therein. This permits easy release of the monitoring device together with the housing part from the inhaler, so that the monitoring device can very easily be switched on, programmed, reset and/or read out—separately from or independently of the inhaler—and/or so that it is very easy to carry out total replacement of the monitoring device together with the housing part or retrofitting of an inhaler with a monitoring device, provided that the housing part is compatible.

The monitoring device or the inhaler may comprise an actuator in order to initiate the nebulisation of fluid automatically when an inhalation is determined or detected, i.e. to carry out breath-controlled nebulisation, and/or temporarily block actuation of the inhaler or nebulisation, for example in order to adhere to a waiting time or avoid overdosing.

The above-mentioned aspects of the present invention and the further aspects of the present invention that will become apparent from the following description may be implemented independently of one another, but also in any desired combination.

The present invention relates in particular to a so-called soft-mist-inhaler (SMI), i.e. an inhaler which produces a spray mist (aerosol) that spreads out relatively slowly. Inhalers of this kind for the purposes of the present invention are, in particular, inhalers in which an aerosol is delivered at a speed of less than 2 m/s, preferably about 1.6 m/s or less and most particularly preferably less than 1 m/s, (measured in each case at a spacing of 10 cm from a delivery nozzle) and/or wherein the delivery or nebulisation of a dose—of preferably 10 to 50 μl of a medicament preparation—lasts longer than 0.7 s, more particularly about 1 s or longer.

Further advantages, features, properties and aspects of the present invention arise from the following description of preferred embodiments with reference to the drawings, wherein.

In the figures, the same reference numerals have been used for identical or similar components, where corresponding or comparable properties and advantages are obtained even though the associated description is not repeated.

Figure 1:
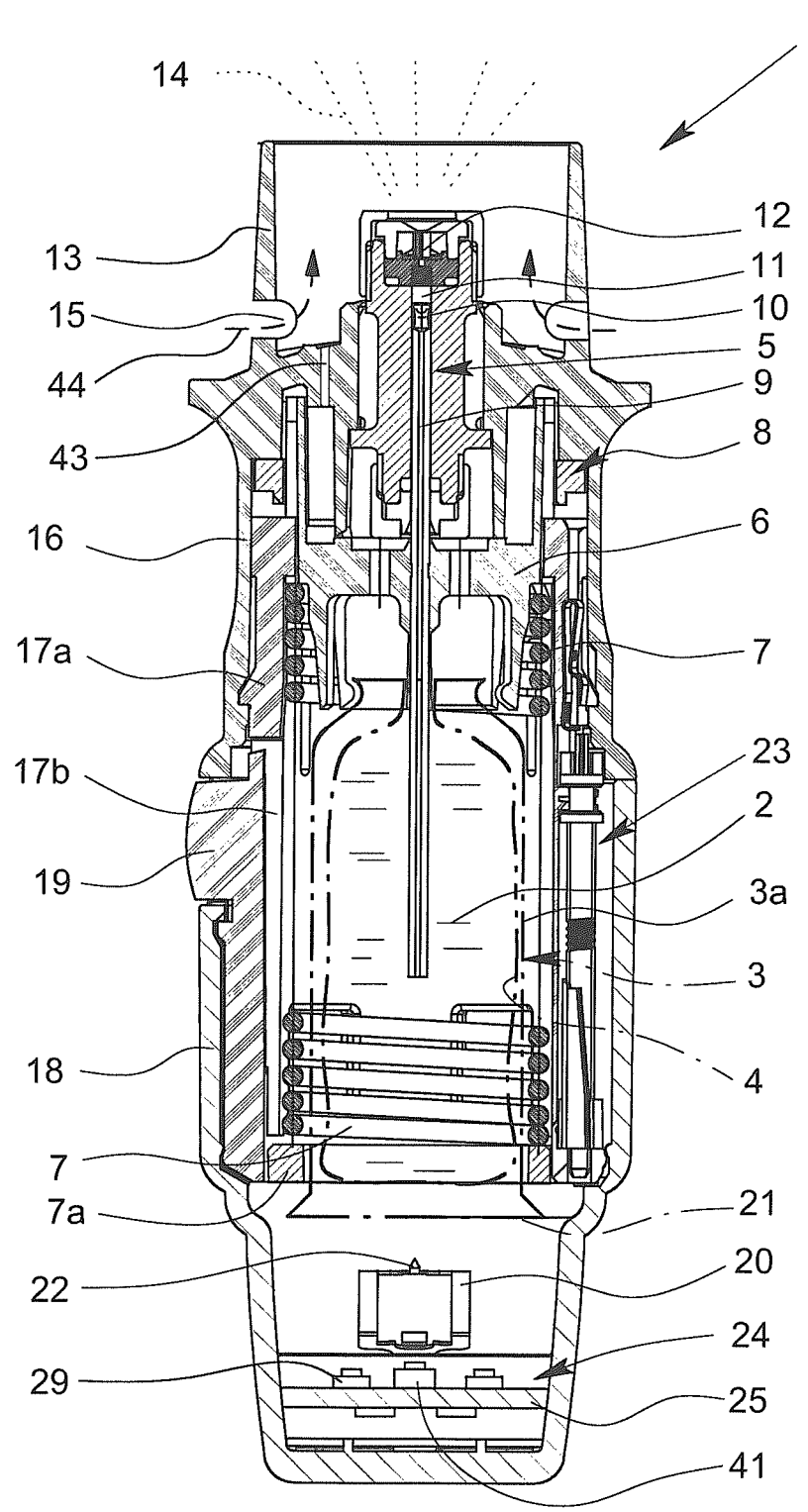
FIG. 1 is a schematic section through a proposed inhaler according to a first embodiment in the untensioned state.
Figure 2:
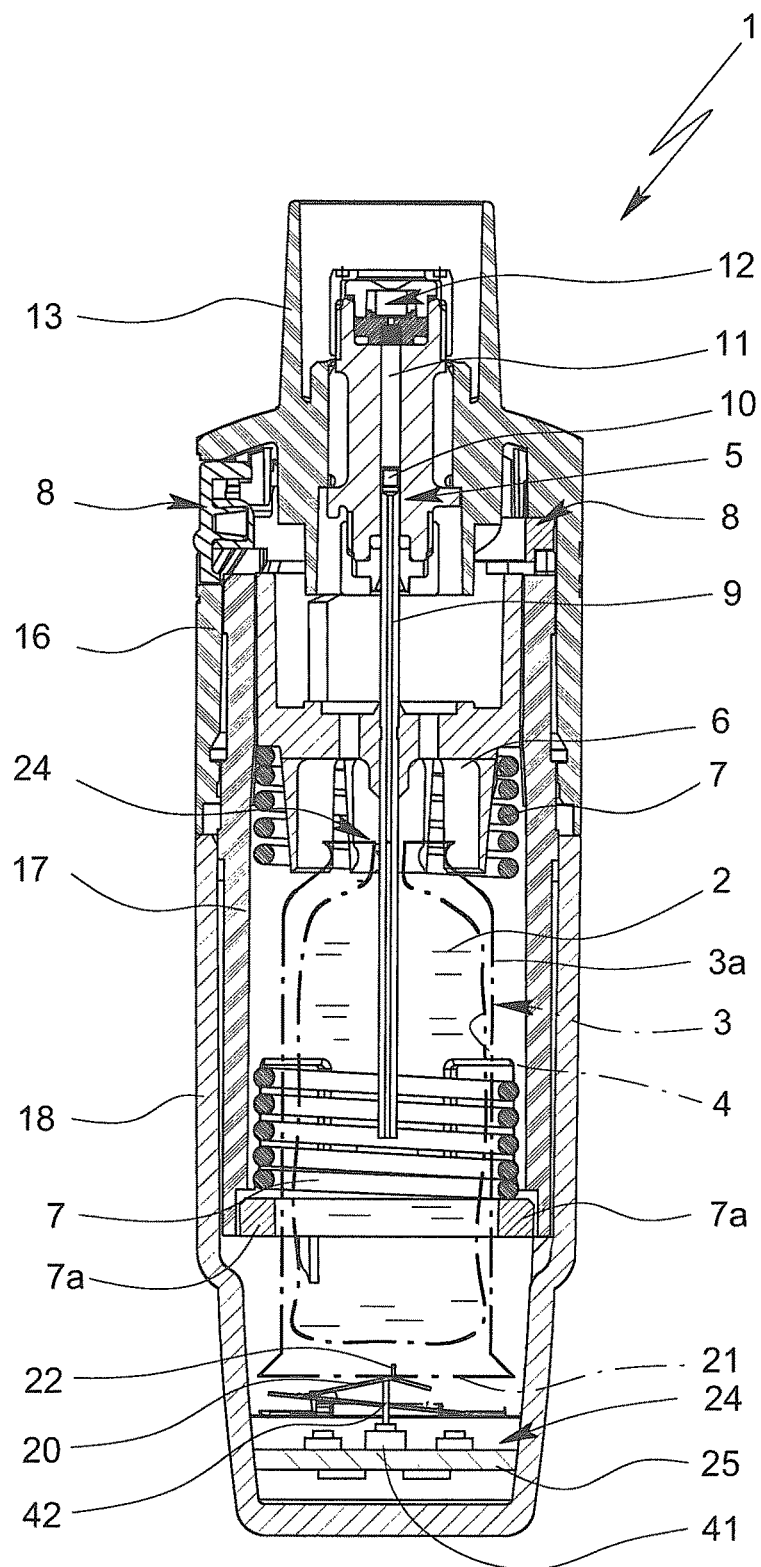
FIG. 2 is a schematic section, rotated through 90° compared with FIG. 1, through the inhaler in the tensioned state.

FIGS. 1 and 2 show a proposed inhaler 1 for nebulising a fluid 2, particularly a medicament preparation, a highly potent drug or the like, in a schematic representation in the untensioned state (FIG. 1) and in the tensioned state (FIG. 2).

The inhaler 1 is constructed in particular as a portable inhaler and/or preferably operates without propellant gas.

During the nebulisation of the fluid 2, preferably a liquid, a respirable aerosol 14 (FIG. 1) is formed which can be breathed in or inhaled by a user or patient (not shown). Normally, inhalation takes place at least once a day, but particularly several times a day, preferably at specified intervals of time, more particularly depending on the complaint.

The inhaler 1 is constructed in particular as a soft mist inhaler as described hereinbefore.

The inhaler 1 comprises a preferably insertable and optionally exchangeable container 3 holding the fluid 2. The container 3 thus forms a reservoir for the fluid 2. Preferably, the container 3 contains a sufficient quantity of fluid 2 for multiple application or several doses of the fluid 2, particularly for a predetermined period of administration, such as a month, or for at least 50, preferably at least 100, doses or nebulisations.

The container 3 is preferably substantially cylindrical or cartridge-shaped and/or may be inserted in the inhaler 1 from below, for example, after the inhaler has been opened, and may optionally be replaceable. It is preferably of rigid construction, the medicament preparation 2 being held in a collapsible bag 4 in the container 3. A typical container 3 as disclosed in WO 96/06011 A1 holds a volume of about 2 to 10 ml. With regard to the preferred construction of the container 3 reference is additionally made to WO 00/49988 A2.

The inhaler 1 preferably has a conveying device or a pressure generator 5, for conveying and atomising the fluid 2, particularly in a predetermined, optionally adjustable metering quantity, i.e. for metered nebulisation or nebulisation in a plurality of defined doses. One dose is delivered on each actuation of the inhaler 1.

The inhaler 1 or pressure generator 5 is particularly designed so that the conveying, pressure generation and/or nebulisation take place without the use of propellants, mechanically and/or by the energy or force of an energy store, particularly a spring store, most preferably by the spring force of a drive spring 7, in the embodiment shown. However, other design solutions are also possible.

The inhaler 1 or pressure generator 5 comprises in particular a holder 6 for the container 3, the associated drive spring 7, which is only partly shown, preferably having an associated trigger element 8 which is manually operable to release it, a conveying element, preferably a conveying tube 9 in the form of a capillary, with an optional valve, particularly a non-return valve 10, a pressure chamber 11 and/or an expulsion nozzle 12, particularly in the region of an outlet or mouthpiece 13.

The container 3 is fixed in the inhaler 1 by means of the holder 6, particularly by a clamping or latching action, such that the conveying tube 9 protrudes into the container 3. The holder 6 may be constructed such that the container 3 can be exchanged.

For tensioning the drive spring 7 the inhaler or pressure generator 5 preferably comprises a tensioning device. When the drive spring 7 is axially tensioned, the holder 6 with the container 3 and the conveying tube 9 is moved downwards in the figures and the fluid 2—or more precisely the next dose—is sucked out of the container 3 into the pressure chamber 11 of the pressure generator 5 through the non-return valve 10.

During the subsequent relaxation of the drive spring 7 after operation of the trigger element 8, the medicament preparation 2 in the pressure chamber 11 is placed under pressure by moving the conveying element or conveying tube 9 back up, with the non-return valve 10 now closed, by releasing the tension on the drive spring 7, so that this conveying tube 9 now acts as a pressure ram. This pressure expels the fluid 2 through the expulsion nozzle 12, where it is nebulised into the preferably respirable aerosol 14, as shown in FIG. 1.

The user or patient (not shown) can inhale the aerosol 14, while preferably supply air can be sucked into the mouthpiece 13 through at least one supply air opening 15, as indicated by dotted arrows 44 in FIG. 1.

During the nebulisation process, which is independent of the inhalation or respiration by the user, the container 3 is moved back into its original position by the drive spring 7. The container 3 thus performs a lifting movement during the tensioning process and during the nebulisation process.

The inhaler 1 comprises in particular a first housing part (upper part) 16 and an inner part 17 which is rotatable relative thereto (FIG. 2) having an upper part 17a and a lower part 17b (FIG. 1), while a second housing part (lower part) 18, which is in particular manually operable or rotatable, is releasably attached, in particular pushed onto the inner part 17, preferably by means of a safety closure or retaining element 19. In particular, the safety closure or retaining element 19 is constructed such that accidental opening of the inhaler 1 or removal of the second housing part 18 is prevented. In particular, in order to release the second housing part 18, the retaining element 19 has to be pressed in against a spring force. In order to insert and/or replace the container 3, the second housing part 18 can be detached from the inhaler 1. The second housing part 18 preferably forms a cap-like lower housing part and/or engages around or over a lower free end portion of the container 3. The drive spring 7, which is only partly shown, is held in the rotatable inner part 17 preferably by means of a ring 7a and/or acts axially preferably between the inner part 17 or ring 7a on the one hand and the axially movable holder 6 on the other hand.

The second housing part 18 can be rotated relative to the first housing part 16, whereby the inner part 17 is also rotated. In this way the drive spring 7 is tensioned in the axial direction by means of a gear (not shown in detail) acting on the holder 6, which acts in particular via a screw thread on the holder 6 or indirectly or directly.

During tensioning the container 3 is moved axially downwards or with its end portion (further) into the second housing part 18 or towards the end face thereof, until the container 3 assumes an end position shown in FIG. 2. In this state the drive spring 7 or inhaler 1 is clamped and locked.

In the embodiment shown, the tensioning device for tensioning the drive spring 7 or other energy or spring store comprises, in particular, at least one rotatable part (actuating part), such as the second housing part 18 and/or inner part 17 and in this case preferably also the gear for converting the rotary movement into the linear, in this case axial, tensioning movement. Preferably, the rotary movement is always continued in the same direction of rotation during tensioning; therefore, reverse rotation is not required. However, other design solutions are also possible.

The two housing parts 16 and 18 preferably together form the housing or an outer housing of the inhaler 3. Preferably, the mouthpiece 13 is formed on the upper housing part 16 or is formed thereby. The lower housing part 18 is preferably arranged on the end of the inhaler 1 opposite the delivery end or the mouthpiece 13. At this opposite end the inhaler 1 or its housing may also be capable of being opened, particularly for the insertion of the container 3. The actuating member for tensioning the inhaler 1 or the drive spring 7 is preferably also located at this opposite end. This actuating member is formed by the housing part 18 in this case, as explained hereinbefore.

The inhaler 1 preferably has a device for forcibly ventilating the container 3. When tensioning first takes place, the container 3 is preferably pierced or opened in its base. In particular, an axially acting spring 20 arranged in the housing part 18 comes to abut on the container base 21 and, with a piercing element 22, pierces the container 3 or an in particular gastight seal provided in the base for ventilation purposes when contact is first made.

The device for forcible ventilation is thus formed in this case by the piercing element 22, which is held or formed by the spring 20. However, other design solutions are also possible.

It should be noted that during the piercing for ventilation purposes only the preferably rigid outer shell 3a of the container 3 or a related seal or the like is opened. The bag 4 containing the fluid 2 remains undamaged. As the fluid 2 is removed from the bag 4 through the conveying tube 9 the flexible bag 4 collapses. For pressure equalisation, ambient air can flow into the container 3 through the ventilation or piercing opening.

In order to use the inhaler 1, first of all the container 3 has to be inserted. This is preferably done by removing or pulling out the second housing part 18. The container 3 is then axially inserted or pushed into the inner part 17. At the same time the container 3 is opened at the head end or attached. This is done by means of the conveying element, i.e. the conveying tube 9, which pierces a seal preferably provided at the head end of the container 3 and is then inserted through a septum at the head end of the container 3 into the interior of the bag 4. Thus the fluidic connection between the container 3, or more accurately between the bag 4 in the container 3, via the conveying tube 9 to the pressure generator 5 or pressure chamber 11 is produced.

Then the second housing part 18 is pushed on again. The inhaler 1 can now be tensioned for the first time. At this stage the container 3 is then pierced at its base by the piercing element 22, i.e. forcibly ventilated, as explained previously.

After the container 3 has been inserted and fluidically connected and before it is used for the first time, the inhaler 1 is preferably tensioned and triggered several times. As a result of this so-called priming any air present in the conveying tube 9 and in the pressure generator 5 is displaced by the fluid 2 to the expulsion nozzle 12. The inhaler 1 is then ready for inhalation.

The quantity of fluid 2 delivered per spray or nebulisation process is preferably about 10 µl to 50 µl, more particularly about 10 µl to 20 µl, most preferably about 15 µl.

The drive spring 7 is preferably installed in a biased state in order to achieve a high spring pressure. In fact, in the proposed inhaler 1 the pressurisation and conveying of the fluid 2 during the nebulisation process takes place preferably only by spring force, and more particularly only by the force of the drive spring 7.

The inhaler 1 is preferably constructed such that the fluid 2 in the pressure generator 5 or in the pressure chamber 11 reaches a pressure of 5 MPa to 60 MPa, particularly about 10 MPa to 50 MPa during delivery. Particularly preferably, during the delivery or nebulisation, a pressure of about 5 MPa to 60 MPa, more particularly about 10 to 30 MPa, is reached at the expulsion nozzle 12 or at the nozzle openings thereof. The fluid 2 is then converted into the aerosol 14, the droplets of which have an aerodynamic diameter of up to 20 µm, preferably about 3 µm to 10 µm. The nebulising activity or nebulising effect is achieved or further assisted by preferably intercepting jets delivered by the expulsion nozzle 12.

The inhaler 1 is preferably constructed such that the aerosol 14 is delivered at low speed, particularly at a speed of less than 2 m/s, most preferably about 1.6 m/s or less (in each case measured at a distance of 10 cm from the expulsion nozzle 12). The inhaler 1 is thus preferably in the form of an SMI. The low dispensing speed can be obtained or assisted by intercepting jets of the fluid 2, which are delivered by the expulsion nozzle 12 and/or by a suitable choice of spring force.

Particularly preferably, the construction of the inhaler 1 is such that the aerosol generation lasts for more than 0.7 s, preferably substantially 1 s or longer, in particular for more than 1.5 s. The time taken to nebulise a dose or to actuate the inhaler 1 is thus preferably more than 0.75, more particularly about 1 s or more. The inhaler 1 preferably comprises a counter 23 as schematically shown in FIG. 1. The counter 23 preferably operates purely mechanically and/or counts the tensioning of the inhaler 1 or the drive spring 7. For example the counter 23 comprises a threaded spindle with an associated slider, the threaded spindle preferably being drivable by the rotation of the inner part 17 relative to the upper housing part 16. However, other design solutions are also possible.

The inhaler 1 preferably comprises a monitoring device 24 for detecting uses of the inhaler 1. The monitoring device 24 in the first embodiment shown is preferably installed in the inhaler 1 or its housing, particularly preferably in the actuating member or housing part 18, as indicated in FIGS. 1 and 2.

The monitoring device 24 is preferably fixedly installed and/or cast, glued or clipped into the housing part 18. However, other design solutions are also possible.

The monitoring device 24 preferably forms a module or unit.

The monitoring device 24 preferably comprises, in the embodiment shown, a printed circuit board 25 with components mounted thereon.

The monitoring device 24 preferably operates electronically.

Figure 3:
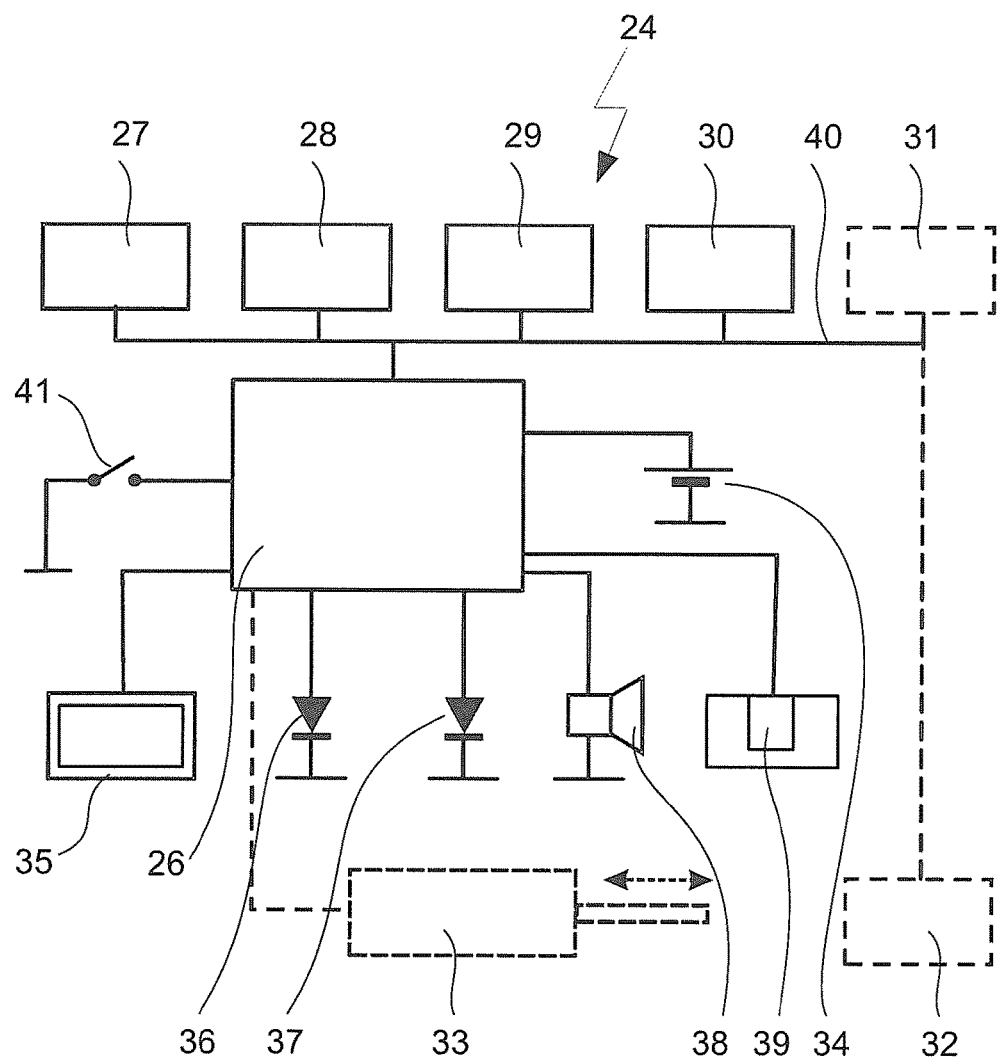
FIG. 3 is a block circuit diagram of a monitoring device of the inhaler.
Figure 4:
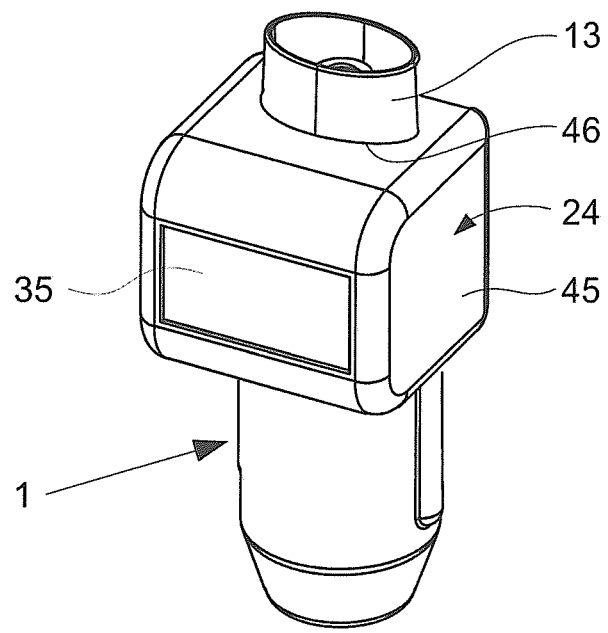
FIG. 4 is a perspective front view of a proposed inhaler with a coupled or added monitoring device according to a second embodiment.
Figure 5:
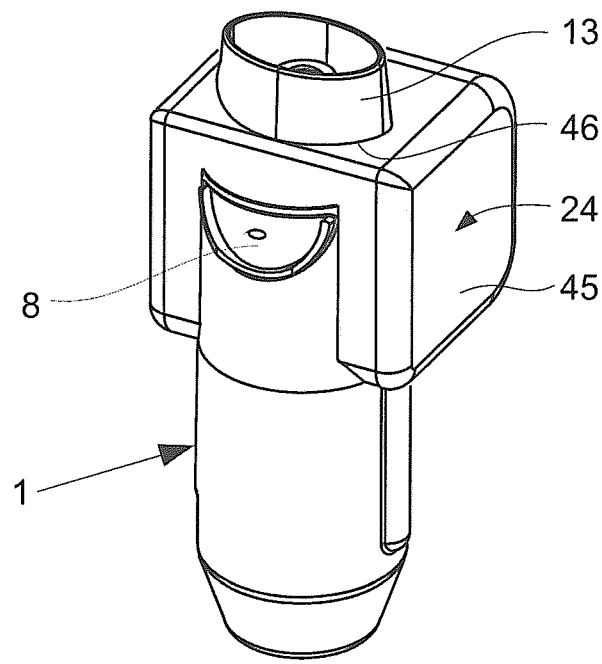
FIG. 5 is a perspective rear view of the inhaler according to FIG. 4.
Figure 6:
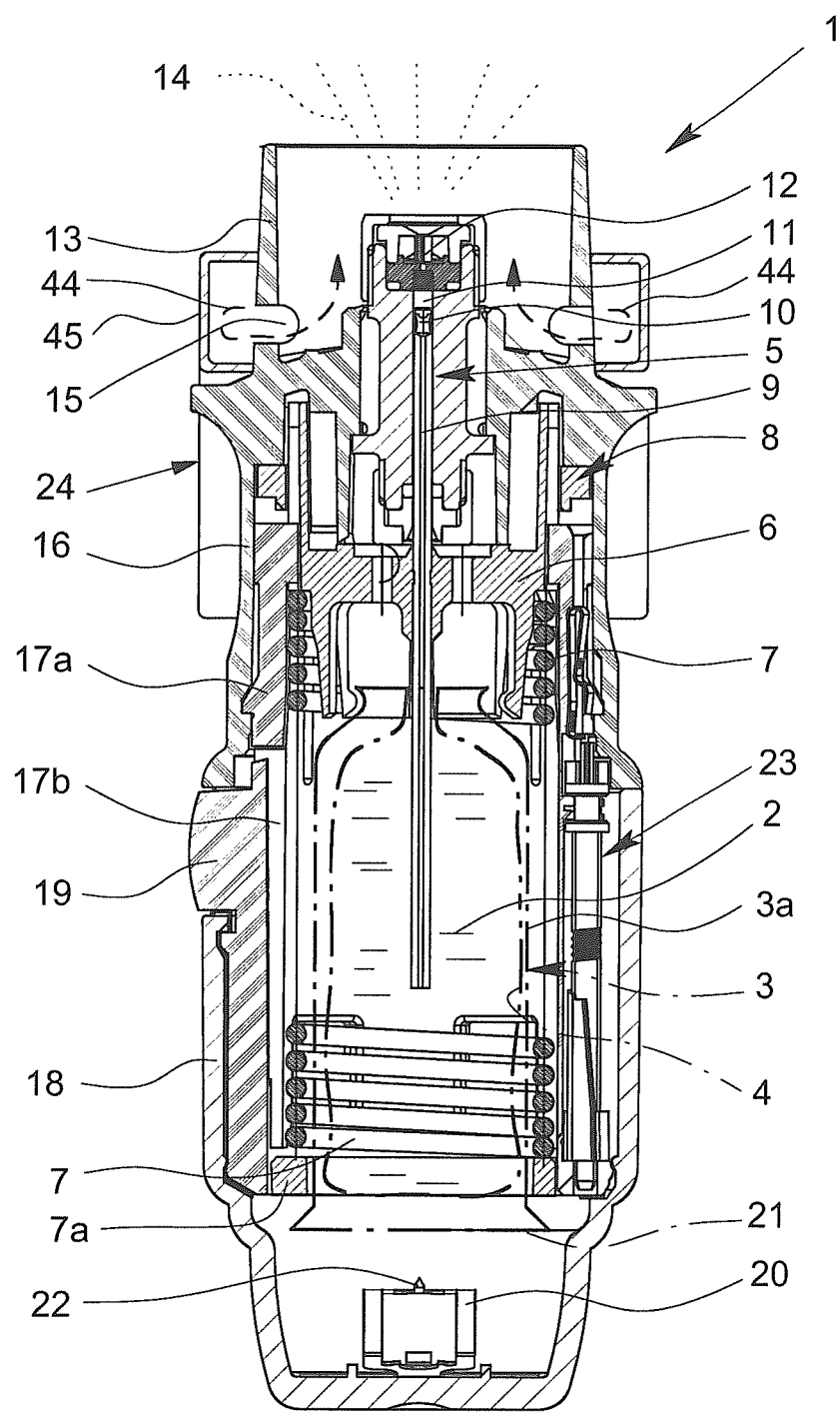
FIG. 6 is a schematic section through the inhaler according to FIG. 4 in a section plane corresponding to FIG. 1.
Figure 7:
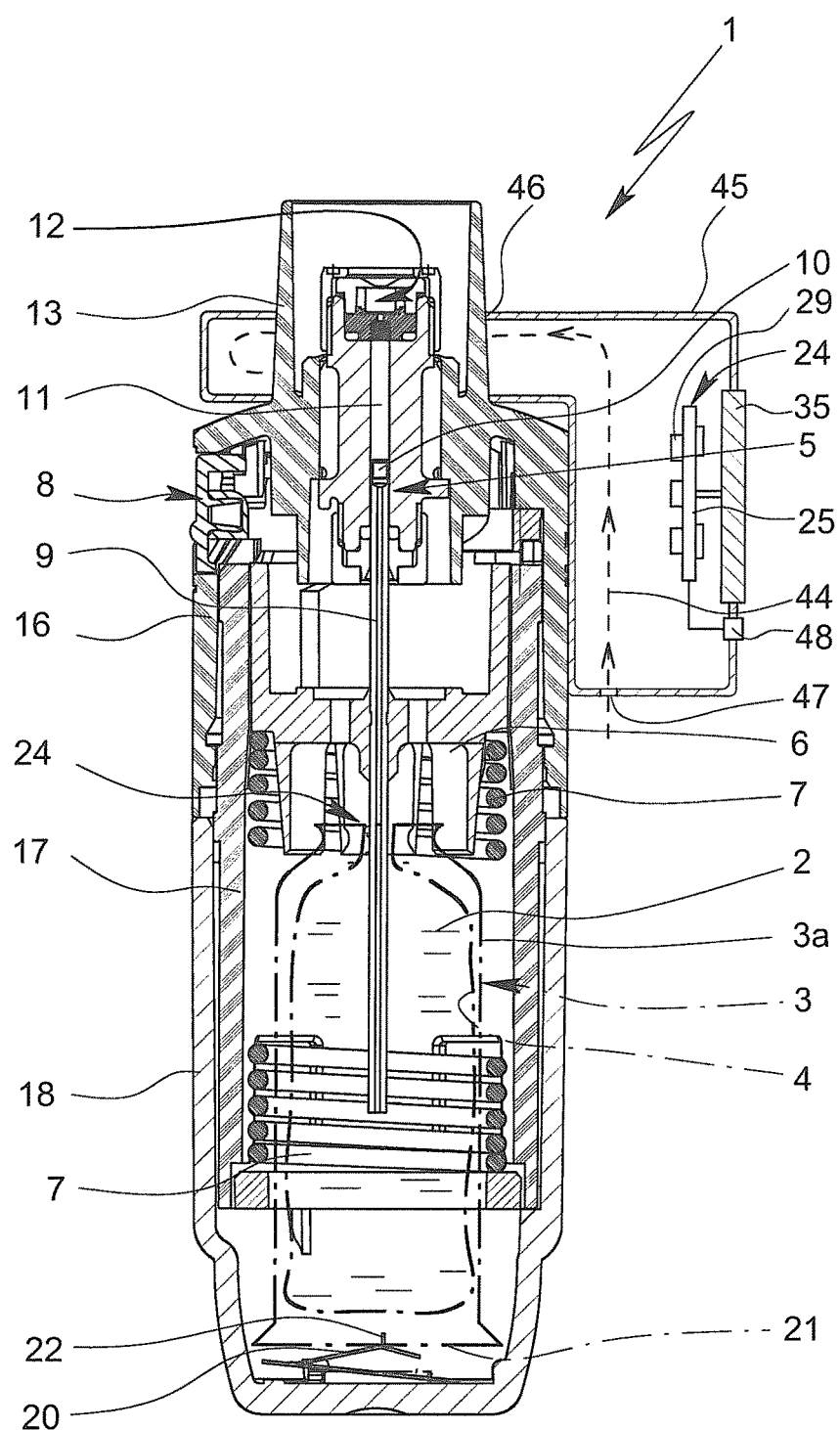
FIG. 7 is a schematic section through the inhaler according to FIG. 4 in a section plane corresponding to FIG. 2.

A preferred construction of the monitoring device 24 is described in more detail hereinafter with reference to the schematic block circuit diagram shown in FIG. 3.

The monitoring device 24 preferably comprises a processor or microcontroller 26 for controlling the monitoring device 24, a time base or clock 27 (which may also be a timer or the like), a memory 28, a sensor 29 for measuring measured values corresponding to the current of supply air or dependent thereon, particularly pressure values (in the form of a pressure sensor in the embodiment shown), and/or at least one position sensor.

The monitoring device 24 preferably has at least one position sensor, in this embodiment two position sensors, namely an acceleration sensor 30 and/or a GPS sensor 31, in particular.

The memory 28 is preferably non-volatile and/or rewritable.

The acceleration sensor 30 is, for example, a preferably three dimensionally measuring so-called MEMS-gyro-sensor. A sensor of this kind is able to detect the acceleration of the earth, for example, and thereby make it possible to detect the orientation of the inhaler 1. Moreover, accelerations can be measured or detected in every three dimensional direction using a sensor of this kind. A path of movement of the inhaler 1 can be determined from these acceleration values taking account of the respective times. This determination may take place, as desired, in the monitoring device 24 or subsequently, by means of the corresponding data and information outside the monitoring device 24 or outside the inhaler 1.

Acceleration sensors of this kind are used for example in cars, particularly for activating airbags in the case of accidents, and are therefore available at low cost. The GPS sensor 31 makes it possible to detect the position of the inhaler 1 on Earth. The sensor 31 makes use of the so-called Global Positioning System. However, position can be determined by any other suitable method.

The charging of an accumulator preferably takes place by induction.

Particularly preferably the temperature measurement or detection is carried out directly by means of the pressure sensor 29. Combined sensors of this kind are available at low cost. However, once again other solutions or constructions are possible.

The monitoring device 24 preferably also comprises a temperature sensor, a moisture sensor 32 and/or an actuator 33.

The monitoring device 24 preferably also comprises an energy or current supply 34, particularly in the form of an accumulator or a battery, preferably a button-cell and/or comprising a photo-electric cell or solar cell or the like.

The monitoring device 24 or inhaler 1 preferably comprises at least one display device particularly an optical display device, particularly preferably a digital or other display such as a monitor screen or a display (display field) 35, preferably in the form of an LCD display, and/or at least one light-emitting diode, or a plurality of light emitting diodes 36 and 37 with different colours, as required, and/or an acoustic indicating means such as a loud speaker, buzzer 38 or the like.

The monitoring device 24 or the optical display 35 may if necessary also act as a dosage counter, particularly to indicate the number of doses of fluid 2 that have already been dispensed or are still to be dispensed.

When the flow resistance is known, the flow rate of the breathing, i.e., the flow speed when breathing in or the volume flow during breathing in can be determined from the pressure measurement.

The monitoring device 24 preferably comprises an interface 39 for the transmission of data, particularly for inputting or outputting data, particularly for outputting data relating to the use of the inhaler 1. The interface 39 preferably operates optically or in the infrared range. This is particularly secure against unwanted listening-in or eavesdropping. However, the data transmission may also be effected by any other method, for example by radio or electrical contact of the transmission device 24 or printed circuit board 25 or via another electrical connection such as a plug or the like. For the issuing or transmission of data it is also possible to use generally known or special protocols or interfaces such as Bluetooth, USB, SATA or the like. Alternatively or additionally, the inductive transmission of data is also possible.

Preferably, most or all of the components and parts of the monitoring device 24 are arranged on the printed circuit board 25 or connected thereto. However, individual components or parts may also be arranged separately from it, particularly an optical display device such as the display 35 and/or the actuator 33 or the like. These parts or components are then preferably electrically connected to the transmission device 24 or printed circuit board 25 and/or are actuated accordingly by the transmission device 24.

Individual components of the monitoring device 24, for example the clock 27, the memory 28, the pressure sensor 29, the position sensors and/or the moisture sensor 32, are preferably connected to the micro-controller 26 via a bus 40. However, connection may be made by some other means.

The inhaler 1 or monitoring device 24 preferably comprises a sensor or switch 41 for switching on, waking up and/or activating the monitoring device 24.

Particularly preferably, the monitoring device 24 is woken up, switched on or activated when the drive spring 7 of the inhaler 1 is tensioned and/or when a certain position of the container is reached, more particularly the bottom end position of the container or the position that the container 3 occupies when the inhaler 1 is tensioned (as shown in FIG. 2). This is carried out, particularly preferably, by the switch 41 being actuated and/or formed by the container 3 or the spring 20 associated with the container 3. For example, the spring 20 may form or comprise an electrical contact which opens and closes depending on the position of the container or the position of the spring 20. FIG. 2 schematically shows how the switch 41 co-operates with the container 3 or spring 20 or can be actuated thereby, for example via a contact or switching pin 42. In particular, the switch 41 is in the form of a microswitch. However, any other suitable contact, switch or the like may be used here. Furthermore, the switch 41 may also be formed by a different sensor or the like. In particular, the switch 41 in the sense of the present invention forms a sensor for waking up or switching on the monitoring device 24 when the drive spring 7 is tensioned or when a certain container position is reached, in this case the end position of the container when the inhaler 1 is tensioned.

The spring 20 may, if required, also form a unit with the monitoring device 24 and/or may be mechanically connected to the printed circuit board 25 or may be supported by or mounted on the latter.

The monitoring device 24 preferably comprises the pressure sensor 29 for measuring the air pressure in the housing of the inhaler 1, particularly reduced pressure or a pressure drop as the user (not shown) of the inhaler 1 breaths in or inhales. The pressure sensor 29 serves to detect a current of supply air and hence an inhalation and thereby detect use of the inhaler 1.

Instead of the pressure sensor 29, however, any other sensor 29 may also be used, particularly a flow sensor or the like. For example, a flow sensor may be incorporated as a sensor 29 of the monitoring device 24 for detecting the flow of supply air into the mouthpiece 13, as disclosed in WO 2005/080001 A1, in particular. This sensor 29 can then be connected to the monitoring device 24 for example via corresponding connections or a cable and/or it may transmit measured values by wireless operation. Alternatively, the monitoring device 24 may also be inserted or incorporated directly in the mouthpiece 13 together with the sensor 29, particularly if it is suitably miniaturised.

In the embodiment shown, however, the sensor 29 used is not a flow sensor but a pressure sensor. Tests have shown that sensors of this kind also make it possible to determine the flow of supply air and thereby detect breathing in or inhalation by a user in a surprisingly effective manner. As pressure sensors are available more cheaply than flow sensors, this results in a simpler and cheaper construction.

Particularly preferably, the pressure sensor 29 is mounted not in the mouthpiece 13 but outside the mouthpiece 13. Particularly preferably, the pressure sensor 29 is arranged in the inhaler 1 or its housing separately from the mouthpiece 29, particularly in a separate spatial region which is fluidically connected to the mouthpiece 13 or a supply air pathway of the inhaler 1. In the embodiment shown, the pressure sensor 29 is arranged in the actuating part or housing part 18. In the embodiment shown, this space is fluidically connected, for example, via a bore or opening 43 in the upper housing part 16 to the mouthpiece 13 or supply air pathway 44 indicated by dotted lines in FIG. 1. The expression "fluidic connection" in the present invention is to be understood as meaning that a gaseous connection is provided which allows a sufficiently good equalisation of pressure and hence pressure measurement. Thus, the pressure sensor 29 preferably provides a measurement or detection of a reduced pressure in the inhaler 1 or mouthpiece 13 which occurs during inhalation or breathing in by user (not shown) as a result of a throttle effect on the supply air opening or openings 15 for the current of supply air 44.

The spatial separation of the pressure sensor 29 or other sensor from the mouthpiece 13 or delivering region of the inhaler 1 gives rise to a number of advantages. Unwanted soiling of the sensor 29 can be avoided. Retrofitting of existing inhaler constructions is often easier. The monitoring device 24 may form a module with the sensor 29. This in turn makes construction easier and particularly retrofitting.

If the inhaler 6 is not in use, the monitoring device 24 is preferably switched off, deactivated or in stand-by mode. It is switched on or activated or woken up, for example, by the switching on of the power supply 34. Preferably, the monitoring device 24 is automatically switched on, woken up or activated when the inhaler 1 is used, particularly when a mouthpiece cover (not shown) is opened or when the inhaler 1 or the drive spring 7 is tensioned, most preferably when a predetermined position of the container is reached, particularly the end position or tensioned position of the container 3 shown in FIG. 2, with the inhaler 1 tensioned. Detecting the tensioning of the inhaler 1 or the reaching of a certain position of the container, such as the above-mentioned end position, is preferably done by the means of the sensor or switch 41. If in the embodiment shown the inhaler 1 is brought or transferred from the untensioned state shown in FIG. 1 into the tensioned state shown in FIG. 2, the container 3 or the spring 20 operates the switch 41, particularly by means of the switching pin 42, thereby switching on or waking up or activating the monitoring device 24. However, other design or method solutions are also possible.

After being switched on or activated or woken up, the monitoring device 24 measures the pressure (air pressure) preferably continuously or at short intervals, over and over again, by means of the pressure sensor 29. The monitoring device 24 is thus designed particularly for determining a pressure pattern.

If, after the tensioning of the inhaler 1 or after the monitoring device 24 has been switched on or activated, a user breaths in or inhales through the mouthpiece 13 or other delivery section of the inhaler 1, air is sucked in through the supply air pathway 44. A reduced pressure is thereby produced in the inhaler 1 or mouthpiece 13. This reduced pressure is measured or detected or determined by the pressure sensor 29 which is fluidically or pressure-connected to the supply air pathway 44 or mouthpiece 13 and hence by the monitoring device 24. By suitable calibration it is possible to determine the corresponding flow volume or current of supply air from the pressure pattern or from the reduced pressure that occurs during breathing in or inhaling. Accordingly it is possible to tell whether, how powerfully and/or how long the user breaths in or inhales.

Preferably, the pressure is measured before the nebulisation of the fluid and then again during the fluid nebulisation. The pressure measurement may optionally also take place before the breathing in or inhaling, e.g. sporadically at certain times or when the inhaler 1 is moved. The monitoring device 24 is thus designed in particular to detect a pressure pattern beginning before inhalation and during inhalation and/or nebulisation and/or nebulisation. This is preferably achieved in terms of construction or process by the fact that the pressure values measured by the pressure sensor 29 after the switching on or activation and after optional resetting or calibration of the monitoring device 24 are continuously written or stored in the memory 29 and after a certain capacity or quantity of data has been reached, older memory values can be overwritten again by the most recently measured or detected memory values. This is also known as so-called cyclical storage and can be achieved by using a so-called cyclical buffer or cyclical memory as the memory 28. However, other design solutions or software solutions are also possible.

In the embodiment shown, for example, after the tensioning of the inhaler 1 or after the monitoring device 24 has been switched on or activated, there is a continuous storing of pressure data in the memory 28 operating or formed as a cyclic buffer or cyclic memory. At the same time there is continuous monitoring or checking as to whether the inhaler 1 has been initiated, i.e. whether any nebulisation of fluid 2 is occurring. This is ascertained or detected preferably by means of the sensor or switch 41 in the embodiment shown. After the initiation (by pressing the initiating element 8) the nebulisation stroke is carried out, in the course of which the container 3 moves away from its end position or tensioning position as shown in FIG. 2. This is detected by the switch 41.

The detection of the nebulisation may, however, take place in some other suitable manner, alternatively or additionally. Instead of the switch 41, a proximity sensor may be used, for example. However, it is also possible, for example, for an (additional) switch to be associated with the initiating element 8 or other suitable element of the inhaler 1 in order to detect the start of the nebulisation of fluid 2 or the actual nebulisation of fluid 2 or the triggering of the inhaler 1. It is also possible to provide a spray sensor or moisture sensor or the like in the mouthpiece 13, for example, in order to be able to detect the actual production of the aerosol 14.

After the triggering of the inhaler 1 and/or the start of nebulisation has been detected, preferably measurement of the time of breathing in or inhaling is started. It is thus possible, for example, to detect and/or indicate, by means of the monitoring device 24, whether inhalation has continued for a sufficiently long time.

Alternatively or additionally, the monitoring device 24 can also evaluate and optionally indicate whether and to what extent there has been correct or adequate or proper co-ordination of the actuation of the inhaler 1 or nebulisation on the one hand and the breathing in or inhalation on the other hand.

After the start of the nebulisation or after detecting the initiation of the inhaler 1, the pressure data go on being recorded and stored for a further period, for example, and/or until a certain threshold or a certain proportion of memory values in the cyclical buffer or cyclical memory (which may also be a predetermined memory region within the memory 29) of current memory values has been exceeded after the initiation of the inhaler 1 or the start of nebulisation. For example, an absolute number of memory values or a percentage number of memory values can be provided as a limit. In this way, it is possible to ensure that even before atomisation starts, pressure values measured continue to be stored, i.e. are not overwritten to more recent pressure values. However, other technical or procedural solutions or software solutions are possible here as well.

Preferably, the pressure data and/or flow data or the like formed from them are stored by the monitoring device 24 and/or issued particularly through the interface 39.

In supplementary manner, preferably other data or parameters are detected, stored, indicated and/or issued, in particular the present time of day, date, duration of breathing in or inhalation or the like. These further data may alternatively or additionally also include statistical data or evaluations, for example a lung volume calculated or estimated from the data, the dosage presumably taken by the user, or the like. Moreover, the additional data may also include the time delay between the start of breathing in or inhaling on the one hand and the start of the nebulisation or initiation of the inhaler 1, on the other hand, or other information or sensor values of measured values, particularly of the other sensors of the monitoring device 24.

The further data or information may include in particular relative or absolute times and/or durations between different events such as different uses of the inhaler 1.

Alternatively or additionally, the further data and information may also relate to the position, orientation and/or acceleration of the inhaler 1 or a path of movement of the inhaler 1. Using the position sensor or sensors the monitoring device 24 can preferably detect and correspondingly store and/or indicate an absolute position and/or orientation of the inhaler 1 in space and/or alterations or accelerations or the like relating to it. For example, a path of movement of the inhaler 1 can also be determined from acceleration values or data, taking account of the time of the actual detection or measurement. This provides useful information, for example, with regard to correct handling of the inhaler 1.

Preferably, in the present invention, the expression "detecting uses of the inhaler 1" refers to the measuring, detection, storage, output and/or evaluation of one or more of the above-mentioned data and/or items of information. Particularly preferably, it includes, at least, detecting the breathing in or inhaling and/or detecting actuations of the inhaler 1 or movements of the container 3.

As already mentioned, the various data and information are preferably displayed, stored and/or given out. In particular, they may be provided through the interface 39 and/or by any other suitable method. The output or transmission of data may take place after every use of the inhaler 1 or at any other desired time or event, for example after the emptying of the container 3.

For reading out the data or information, the transmission device 24 may communicate with or be coupled to a corresponding communications or reading device (not shown), particularly via the interface 39. For this purpose the monitoring device 24 or the housing part 18 may be separated from the inhaler 1 as required. The monitoring device 24 may also be designed for user information or user guidance. In particular, user guidance may take the form of an acoustic and/or optical display or the issuing of corresponding data, information and/or instructions. For example, a status or an error or a possibility of improvement can be indicated using the display 35 or some other method. Moreover, the respective status of the monitoring device 24 can be indicated for example by means of the light emitting diodes 36 and 37 or in some other way. The monitoring device 24 can also indicate to the user optically and/or acoustically, for example, how long and/or how powerfully he has to breath in and/or inhale and/or when the end of the (required) inhalation is reached.

In the embodiment shown the housing part 18 is preferably at least partly transparent in construction. Accordingly, an optical display through the housing part 18 may be provided as necessary. Corresponding components such as the display 35 and/or the light emitting diodes 36 and 37 may therefore be arranged directly on the printed circuit board 25.

The initiation of the inhaler 1 or drive spring 7 or the start of the nebulisation may also take place automatically, if necessary, in the embodiment shown, particularly if the monitoring device 24 detects (sufficiently strong) breathing in or inhalation by the user. In this the monitoring device 24 or the micro-controller 26 may initiate the nebulisation of fluid 2 via the optional actuator 33, for example. For this purpose the actuator 33 may release the tension on the drive spring 7 or actuate the initiating element 8 accordingly. In this way, breath-controlled nebulisation can be achieved.

Alternatively or additionally, the actuator 33 and/or another optional actuator may also be used to prevent further actuation or triggering of the inhaler 1, for example at the end of a specified period of use or after a certain predetermined number of doses has been given, and the inhaler 1 is then controlled accordingly by the monitoring device 24. Blocking may alternatively or additionally be provided, for example, as a temporary measure to prevent overdosing, particularly when active substances with an addictive potential are being administered.

The housing of the inhaler 1 or the lower housing part 18 is preferably sealed off from the housing part 16 by means of corresponding seals or the like (not shown), particularly relative to the housing part 16, such that the pressure that can be measured by the pressure sensor 29 at least substantially corresponds to the pressure in the mouthpiece 13 or supply air pathway 44. Besides a "sufficient" seal this may also be achieved or at least assisted by correspondingly large connecting cross-sections, particularly between the mouthpiece 13 and the spatial region in which the pressure sensor 29 is located, and, in the embodiment shown, particularly by a sufficiently large opening 43.

Preferably the monitoring device 24 is constructed so that it automatically switches off or is deactivated or goes into standby mode after a certain (first) period of time, starting from the nebulisation or triggering of the inhaler 1. If after the tensioning of the inhaler 1 there is no nebulisation or triggering, automatic switching off, deactivation or switching to standby mode preferably also takes place after a (second) period of time has expired after the waking up or activation of the monitoring device 24, i.e., after the detection of the tensioning of the inhaler 1 or the predetermined container position. If then the inhaler 1 or fluid nebulisation is still initiated, the monitoring device 24 may optionally be switched on or activated or woken up again.

Alternatively or additionally, the monitoring device 24 may be activated or woken up or the power supply 34 may be switched on by the detection of movement of the inhaler 1 (particularly if a change in the position and/or orientation of the inhaler 1 is detected), particularly by means of the acceleration sensor 30 or by means of another jolt or shake sensor.

Preferably, the temperature and/or moisture values which are optionally additionally measured are used as correction values, particularly for correcting when determining the current of supply air and/or when determining the dose of fluid or active substance taken by the user (so called lung dose). Alternatively or additionally, these values may also be used to provide information as to the actual use or ambient conditions under which the inhaler 1 is used.

The inhaler 1 or monitoring device 24 is preferably also designed to measure, detect, store, determine, evaluate, indicate and/or issue the data, information, numerical values and the like, as described in WO 2005/080001 A1.

Preferred ingredients of the preferably medicinal fluid 2 are listed in particular in WO 2009/047173 A2, which is hereby incorporated in full as a reference. In particular, the fluid 2 may be an aqueous or non-aqueous solution, mixture, formulation with or without solvents, such as ethanol or the like.

LIST OF REFERENCE NUMERALS

Inhaler
2 Fluid
3 Container
3a Outer shell
4 Bag
5 Pressure producer
6 Holder
7 Drive spring
7a Ring
8 Outlet element
9 Conveying tube
10 Non-return valve
11 Pressure chamber
12 Expulsion nozzle
13 Mouthpiece
14 Aerosol
15 Supply air opening
16 Upper housing part
17 Inner part
17a Upper part
17b Lower part
18 Lower housing part
19 Retaining element
20 Spring
21 Container base
22 Piercing element
23 Counter
24 Monitoring device
25 Printed circuit board
26 Microcontroller
27 Clock
28 Memory
29 Pressure sensor
30 Acceleration sensor
31 GPS sensor
32 Moisture sensor
33 Actuator
34 Current supply
35 Display
36 Light emitting diode
37 Light emitting diode
38 Buzzer
39 Interface
40 Bus
41 Switch
42 Switching pin
43 Opening
44 Supply air pathway
45 Housing
46 Recess
47 Inlet
48 Operating element

The invention claimed is:

1. An inhaler, comprising:
an insertable container containing a fluid and disposed within an inhaler housing;
a monitoring device for detecting use of the inhaler, where the monitoring device includes: (i) a pressure sensor for measuring air pressure in the inhaler for detecting inhalation, (ii) a position sensor for detecting at least one of a position, orientation and acceleration of the inhaler to determine a path of movement of the inhaler, in its entirety, through a three-dimensional space, and (iii) a data collection device operating to at least one of store and output pressure data from the pressure sensor and/or position data from the position sensor; and
a separable housing within which the monitoring device, including the pressure sensor and the position sensor, is fixedly installed such that the separable housing, including the monitoring device, is detachable from the inhaler housing.

2. The inhaler according to claim 1, wherein the pressure sensor is arranged outside a supply air pathway and/or mouthpiece of the inhaler housing.

3. The inhaler according to claim 1, wherein the pressure sensor is arranged in an actuating or housing part of the inhaler which is fluidically connected to a mouthpiece of the inhaler housing.

4. The inhaler according to claim 1, wherein the pressure sensor is designed to measure or detect reduced pressure in the inhaler during inhalation.

5. The inhaler according to claim 1, wherein the monitoring device is designed to detect a pressure pattern based on the pressure data from the pressure sensor beginning before a nebulization and/or inhalation.

6. The inhaler according to claim 1, wherein the position sensor is an acceleration sensor or a GPS sensor.

7. The inhaler according to claim 1, wherein the monitoring device comprises a further sensor for switching on the monitoring device in the event of at least one of: (i) tensioning of a drive spring of the inhaler, and (ii) a certain container position being reached.

8. The inhaler according to claim 1, wherein the inhaler housing includes a mouthpiece for delivering nebulized fluid, the mouthpiece comprising at least one supply air opening, and wherein the monitoring device is fitted proximate to the mouthpiece in such a way as to cover the at least one supply air opening.

9. The inhaler according to claim 1, wherein the inhaler housing includes a mouthpiece for delivering nebulized fluid, the mouthpiece comprising at least one supply air opening, and wherein the monitoring device is fitted proximate the mouthpiece and constructed so as to form a supply air pathway.

10. The inhaler according to claim 9, wherein the monitoring device covers any further supply air openings of the inhaler housing or mouthpiece.

11. The inhaler according to claim 1, further comprising a pressure generator for conveying and/or nebulizing the fluid independently of any inhalation and/or while simultaneously moving the container.

12. The inhaler according to claim 1, wherein the monitoring device controls an actuator for triggering a nebulization of fluid when an inhalation or an intake of breath is detected based at least on the pressure data from the pressure sensor.

13. The inhaler according to claim 1, wherein the monitoring device has a cyclical memory for continuously storing the pressure data relating to the inhalation before and during an inhalation or nebulization.

14. The inhaler of claim 1, wherein the separable housing is sealed off such that the pressure that is measured by the pressure sensor substantially corresponds to at least one of a pressure within the mouthpiece and a pressure within an air supply pathway of the inhaler housing.

15. The inhaler according to claim 1, wherein the monitoring device and the position sensor operate to detect and store respective values of at least one of a position, orientation and acceleration of the inhaler at respective times and process the respective values at the respective times to determine the path of movement of the inhaler, in its entirety, through the three-dimensional space.

16. An inhaler, comprising:
an insertable container containing a fluid and disposed within an inhaler housing; and
a monitoring device for detecting use of the inhaler, where the monitoring device includes: (i) a pressure sensor for measuring air pressure in the inhaler for detecting inhalation, (ii) an acceleration sensor operating to measure movement of the inhaler, in its entirety, through a three-dimensional space, (iii) a data collection device operating to at least one of store and output pressure data from the pressure sensor, and (iv) a processing device operating to detect a pressure pattern based on the pressure data from the pressure sensor beginning before a nebulization and/or inhalation,
wherein the monitoring device is adapted to: (i) automatically switch off, deactivate, or switch to standby mode after a predetermined period of time, and (ii) activate out of the switch off, deactivated, or standby mode into an active mode in response to the movement of the inhaler through the three-dimensional space, and
wherein the monitoring device, including the pressure sensor, is fixedly installed in a separable housing outside a mouthpiece of the inhaler housing.

17. The inhaler according to claim 16, wherein the monitoring device controls an actuator for triggering a nebulization of fluid when an inhalation or an intake of breath is detected based at least on the pressure data from the pressure sensor.

18. The inhaler according to claim 17, wherein the monitoring device has a cyclical memory for continuously storing the pressure data relating to the inhalation before and during an inhalation or nebulization.

19. The inhaler according to any claim 16, wherein the monitoring device is configured to automatically switch off, deactivate or switch into the standby mode after the predetermined period of time has expired if, after the activation into the active mode, the monitoring device does not detect any tensioning of the inhaler, triggering of the inhaler, or nebulization.

20. The inhaler according to any claim 16, wherein the monitoring device is configured to activate into the active mode if, after automatically switching off, deactivating or entering the standby mode, fluid nebulization is initiated.

21. The inhaler according to claim 16, wherein the monitoring device and the acceleration sensor operate to detect and store respective values of acceleration of the inhaler at respective times and process the respective values at the respective times to determine the path of movement of the inhaler, in its entirety, through the three-dimensional space.

22. The inhaler according to claim 16, further comprising a mouthpiece for delivering nebulized fluid, the mouthpiece comprising at least one supply air opening, wherein the monitoring device is fitted proximate to the mouthpiece in such a way as to cover the at least one supply air opening.

23. An inhaler, comprising:
an insertable container containing a fluid disposed within an inhaler housing;
a monitoring device for detecting use of the inhaler, where the monitoring device includes: (i) a position sensor for detecting and storing respective values of at least one of a position, orientation and acceleration of the inhaler at respective times and process the respective values at the respective times to determine a path of movement of the inhaler, in its entirety, through a three-dimensional space, and (ii) a data collection device operating to at least one of store and output position data from the position sensor; and
a separable housing within which the monitoring device, including the position sensor, is fixedly installed such that the separable housing, including the monitoring device, is detachable from the inhaler housing.

24. The inhaler of claim 23, wherein the monitoring device further includes a display device and the separable housing includes an at least partially transparent window through which the display device is visible.

25. An inhaler, comprising:
- an insertable container containing a fluid and disposed within an inhaler housing;
- a monitoring device for detecting use of the inhaler, where the monitoring device includes: an acceleration sensor operating to measure and store respective values of acceleration of the inhaler at respective times and process the respective values at the respective times to determine a path of movement of the inhaler, in its entirety, through a three-dimensional space; and
- a separable housing within which the monitoring device, including the acceleration sensor, is fixedly installed such that the separable housing, including the monitoring device, is detachable from the inhaler housing,
- wherein the monitoring device is adapted to: (i) automatically switch off, deactivate, or switch to standby mode after a predetermined period of time, and (ii) activate out of the switch off, deactivated, or standby mode into an active mode in response to the movement of the inhaler through the three-dimensional space.

26. An inhaler, comprising:
- an insertable container containing a fluid and disposed within an inhaler housing;
- a mouthpiece for delivering the fluid in nebulized form;
- a pressure sensor located proximate to the mouthpiece, the pressure sensor for measuring air pressure in the inhaler for detecting inhalation;
- a monitoring device for processing data regarding the measured air pressure from the pressure sensor;
- a wireless data connection receiving the data regarding the measured air pressure from the pressure sensor and providing the data regarding the measured air pressure to the monitoring device; and
- a separable housing within which the pressure sensor is fixedly installed such that the separable housing, including the pressure sensor, is detachable from the inhaler housing.

* * * * *